(12) United States Patent
Herrmann

(10) Patent No.: US 6,207,181 B1
(45) Date of Patent: Mar. 27, 2001

(54) RESERVOIR FOR CONTROLLED ACTIVE SUBSTANCE DELIVERY, AND APPARATUS CONTAINING THE SAME

(75) Inventor: Fritz Herrmann, Rheinheldestrasse (DE)

(73) Assignee: LTS Lohmann Therapie-Systeme GmbH & Co. KG, Neuwied (DE)

( * ) Notice: Subject to any disclaimer, the term of this patent is extended or adjusted under 35 U.S.C. 154(b) by 0 days.

(21) Appl. No.: 08/521,954

(22) Filed: Aug. 31, 1995

Related U.S. Application Data (63) Continuation of application No. 08/167,723, filed on Dec. 15, 1993, now abandoned, which is a continuation of application No. 08/011,101, filed on Jan. 26, 1993, now abandoned, which is a continuation of application No. 07/427,114, filed on Oct. 20, 1989, now abandoned.

(30) Foreign Application Priority Data

Mar. 24, 1988 (DE) .................................................. 38 09 978
Mar. 21, 1989 (WO) .................................. PCT/DE89/00177

(51) Int. Cl.[7] ............................ A61F 13/02; A01N 25/00
(52) U.S. Cl. ......................... 424/448; 424/449; 424/409; 424/401; 424/405
(58) Field of Search ...................................... 424/446, 447, 424/448, 449

(56) References Cited

U.S. PATENT DOCUMENTS 4,849,224 * 7/1989 Chang et al. ......................... 424/448

* cited by examiner

Primary Examiner—Thorman K. Page
Assistant Examiner—Isis Ghali
(74) Attorney, Agent, or Firm—Peter S. Gilster

(57) ABSTRACT

The invention relates to reservoirs with a delivery surface for the controlled delivery of active substances decreasing over the time of use to solid, liquid or gaseous acceptors and whereby at least at one point of the reservoir a cross-sectional surface of the reservoir is parallel to the delivery surface and smaller in area than the delivery surface. The invention also relates to an apparatus for the controlled delivery of active substances decreasing over the time of use, which has at least one reservoir. At least one active substance to be delivered is active in the technical, human and veterinary medical, cosmetic and pest control sectors.

18 Claims, 5 Drawing Sheets

RESERVOIR FOR CONTROLLED ACTIVE SUBSTANCE DELIVERY, AND APPARATUS CONTAINING THE SAME

This application is a continuation of application Ser. No. 08/167,723 filled Dec. 15, 1993, now abandoned, which is a continuation of application Ser. No. 08/011,101, filled Jan. 26, 1993, now abandoned, which is a continuation of application Ser. No. 07/427,114, filled Oct. 20, 1989, now abandoned.

FIELD OF THE INVENTION

The invention relates to a reservoir with a delivery surface for the controlled delivery of active substances decreasing over the time of use to solid, liquid or gaseous acceptors, an apparatus for the controlled delivery of active substances decreasing over the time of use, its manufacture and the use thereof. More specifically, the present invention relates to transdermal therapeutic systems.

BACKGROUND OF THE INVENTION

The term active substances in the present context is understood to mean substances having a desired action, of either an optical, physical or chemical/biological nature, in a field of technology, medicine or biology, including pest control.

The delivery of active substances therefrom to a specific acceptor medium can take place in two ways with respect to the time function.

On the one hand the total desired active substance quantity can be supplied in a single portion and on the other hand the desired total quantity can be supplied discontinuously or continuously, subdivided into partial quantities of varying magnitude, over a given period of time to the acceptor medium. The present invention deals with the latter case.

The present invention relates to the delivery of active substance from a reservoir to a specific acceptor medium. Apart from the controllability of the active substance quantity delivered in time and in the time unit by the reservoir, it must also be possible here to control the active substance delivery characteristics. This requirement is in many cases unavoidable and e.g. in the case of transdermal, therapeutic systems plays an important part. These are active substance-containing apparatuses or administration forms, which deliver to the skin over a fixed time period and in a continuous manner one or more active substances with a predetermined rate. Considerable efforts have been made to realize these systems.

The aim of obtaining an approximately constant active substance delivery over a desired period of time has been achieved. Solution proposals exist for other active substance delivery characteristics which have not, however, been fully satisfied. Thus, use must be made of the composition of the reservoir matrix in connection with a controlled decrease in the active substance delivery over the administration period (in the case of medicaments this decrease is e.g. sought in the case of cortisone-containing products, as well as in nitroglycerin administration, but may also be necessary for adapting to the biorhythm of the organism under treatment). However, this only offers a limited scope, because it is also necessary to fulfil the basic requirement of the diffusability of the active substance in the matrix. The concentration and/or concentration distribution of the active substance in the matrix also offer possibilities of control in the desired sense, but can only be used in special cases.

U.S. Pat. No. 4,564,364 proposes subdividing the active substance reservoir into volume areas, in which the active substance concentration is partly above and partly below the saturation concentration. Through a planned geometrical design of the volume areas, it is possible to influence the active substance delivery characteristics. Quite apart from the fact that the production of such systems is complicated and costly, it does not disclose the present technical teaching of solving the problem of a planned, controlled decrease in the active substance delivery over the administration or application time of the system.

Another way for controlling the active substance delivery from matrix reservoirs is given in German Patent 33 15 272. In this case the reservoir comprises at least two layers parallel to the delivery surface, which contain concentrations above the saturation concentration, the concentration increasing with increasing distance of the layer from the delivery surface. This admittedly makes it possible to keep the delivery rate at a given level for this desired time, but here again it is not possible to achieve a planned control of the decrease in the active substance delivery rate. EP-A-0 227 252 describes an active substance delivery characteristic particularly in connection with transdermal therapeutic systems, in which with the aid of an enhancer, it is possible to set a high delivery rate over a first part of the administration period, with a much lower delivery rate over a second part of said period. The construction and composition of the reservoir are very complicated and must be determined for each individual case on the basis of time-consuming preliminary tests. In addition, this system is limited to a two-stage active substance delivery characteristic.

SUMMARY OF THE INVENTION

The problem of the present invention is to permit a widely usable, clearly defined control decrease in the active substance delivery over a desired or necessary time.

Surprisingly the solution of this problem is found in that at least at one point the reservoir is provided a cross-sectional surface of that point of the reservoir which is smaller than the delivery surface and which is parallel thereto.

Advantageous further developments of the invention can be gathered from the dependent claims.

The delivery quantity of a substance over a period of time from a reservoir with a delivery surface is directly proportional to the size of the latter. The reservoir can be made from pure active substance or a reservoir material kept unchanged over the period of use and in which active substance is distributed. In the former case the delivery of the active substance leads to a wearing away of the reservoir, so that new delivery surfaces are constantly formed. If the cross-section of the reservoir parallel to the delivery surface is now reduced at at least one point, a size-reduced delivery surface is formed there, so that the active substance delivery is decreased.

In the latter case of a reservoir material with the active substance distributed therein, the conditions are different. The delivery surface formed during the manufacture of the reservoir is maintained in its entire size over the entire administration period. The active substance passing through it leaves behind in the reservoir a zone parallel to the delivery surface with a reduced active substance concentration compared with the remainder of the reservoir and whose further dilution is avoided by a subsequent supply of active substance from the more highly concentrated reservoir part. Thus, the quantity delivered through the delivery surface is defined by the extent of the subsequently supplied active substance, so that the thickness of the zone constantly increases with reduced concentration. Thus, parallel to the delivery surface is formed a type of separating surface between the reservoir parts with reduced concentration and increased original concentration, whose spacing with respect to the delivery surface constantly rises during administration and whose size corresponds to the reservoir cross-section parallel to the delivery surface. The size of this separating surface and therefore the cross-section of the reservoir consequently determines the delivery rate of active substance through the delivery surface. According to the invention the size of the separating surface is defined by a corresponding geometrical configuration of the reservoir and is reduced in planned manner, so that the delivery quantity of active substance from the reservoir is reduceable in a clearly defined and controlled manner compared with the initial quantity.

The cross-sectional reduction can also be continuously adjusted over the entire reservoir and there can be a difference in a linear or non-linear pattern of the reduction. If necessary, it is also possible to achieve a discontinuous, e.g. step-like cross-sectional reduction. Here again, the pattern can be linear or non-linear.

Appropriate geometrical shapes for the reservoir are e.g. cones, truncated cones, pyramids, truncated pyramids, tetrahedrons, truncated tetrahedrons, hemispheres, spherical segments and spherical layers. The reservoir can naturally also be designed in such a way that the cross-sectional reduction only takes place in part of the reservoir. Symmetry elements in the reservoir are not unavoidable conditions for the inventive solutions of the problem. In view of the large size of the reservoir, the delivery surface can have a maximum extension in one direction and this can be up to 100 times(x) the extension in the direction at right angles thereto. In the special cse of a rectangular delivery surface, this corresponds to a 100x greater length and width.

In order that only a specific outer face of the reservoir takes over the function of active substance delivery, at least one layer impermeable for the reservoir components is fixed to all the other surfaces. The reservoir can also be at least partly housed in a corresponding depression in a carrier material and can be fixed in said depression by at least one surface, excepting the delivery surface. In order to be able to precisely fix the start of active substance delivery and protect the delivery surface against damage, the delivery surface is preferably protected by an at least one-layer, detachable surface structure, which is impermeable to the reservoir components.

At least one inventive reservoir is a component of an inventive apparatus for the controlled delivery of active substances decreasing over the period of use. In certain cases the combination of several reservoirs can be preferred and they can also differ from one another with regards to their geometrical design. Preferably the apparatuses comprise elements permitting a fixing of the apparatus at the point of application. Presure sensitive adhesive areas of the apparatus have proved particularly suitable for this. The reservoir comprises at least one active substance, which can be delivered to solid, liquid or gaseous acceptor media and the active substance or substances have their action in technology, human and veterinary medicine, cosmetics and pest control. Preference is given to active substances for human medicine in apparatuses referred to as transdermal therapeutic systems.

The reservoir is preferably formed in a corresponding mold for the manufacture of an inventive apparatus. The methods used for this are preferably cooling a melt of the reservoir material, evaporating solvents or dispersants, hot or cold pressing of reservoir material and profile extrusion, or also the crosslinking of polymers by radiation or heat. The enveloping of the reservoir, except the delivery surface, preferably takes place by lamination, spraying and dipping.

Further preferred methods for the manufacture of the inventive apparatuses, in which at least part of the reservoir is received in a carrier material in appropriate depressions comprise the production of the depressions by deep-drawing or stamping, or at the time of shaping the carrier material.

The apparatuses according to the invention are preferably used in technology, human and veterinary medicine, cosmetics and pest control.

A particularly preferred inventive use of the apparatuses is that of transdermal therapeutic systems.

The invention offers extensive possibilities in all cases, where an active substance is to be so delivered from a reservoir to any acceptor medium, that a planned, controlled decrease in the delivery rate is achieved over the administration or application period. Contact between the reservoir and the acceptor medium takes place via the delivery surface. The latter is part of the surface of the three-dimensional reservoir. If the acceptor medium is a solid substance, then the delivery surface must be adapted to the contours of the contact surface of the solid substance, so that a controllable transfer of the active substance is ensured. From the manufacturing standpoint, preference is given to planar delivery surfaces. In the case of liquid and gaseous acceptor media, the design of the delivery surface is mainly defined by the manufacturing possibilities, because these acceptor media can be adapted to any delivery surface shape.

The inventive apparatus comprises at least one of the aforementioned reservoirs. However, in certain cases apparatuses with several reservoirs are advantageous. Thus, in the case of a specific, required delivery characteristic and quantity, the dimensions of the necessary reservoir can be too cumbersome. The delivery surface is then broken down into individual portions, which in turn form the delivery surfaces of several smaller reservoirs, which can be combined in one apparatus. The possibilities of the reciprocal geometrical arrangement of said smaller reservoirs are not limited by the sought delivery characteristics of the active substances.

In other cases it can be appropriate to have several reservoirs in one apparatus when it is a question of using one apparatus for administering two active substances which are incompatible in simultaneous form and in accordance with the same or different delivery characteristics, i.e. reservoirs with different geometrical configurations can be combined.

German utility model 87 09 810.5 describes a medical plaster having geometrically defined troughs in the carrier material and which prior to application are filled with reservoir material, such as e.g. an ointment. The geometrically defined construction of the troughs is intended to more accurately define the volume of the reservoir material used for administration than was possible with the previously conventional means. However, said publication does not disclose a controlled, clearly defined delivery characteristic with respect to the decrease in the active substance delivery over the administration period.

Apart from the geometrical shape of the reservoir selected according to the invention, the delivery characteristics can also be influenced by fixing freely selectable structural elements of said shape. Thus, e.g. the delivery characteristic of a spherical reservoir is dependent on the freely selectable angle in the apex of the cone. In the case of a small angle, a relatively high cone is obtained, which has a relatively gradual decrease in the active substance delivery, whereas in the case of large angles a lower cone is obtained with a rapid active substance delivery rate decrease. This shows the numerous different variants possible with respect to the reservoir design according to the present invention.

The delivery rate, i.e. the quantity of active substance delivered per unit of time, is also determined by other factors. In the case of reservoirs comprising pure active substance or active substance preparation and which are erroded in contact with the acceptor medium, the delivery rate is mainly influenced by the solubility of the active substance or the active substance preparation in the acceptor medium. The second factor is naturally the size of the delivery surface, which plays an important part even in the case of constant volume reservoirs over the administration period. Further parameters are the solubility of the active substance in the reservoir matrix, the active substance concentration in the matrix, the concentration distribution in the matrix and the diffusability of the active substance in the matrix. Mention is finally made of the temperature during the active substance delivery and this makes it appropriate in the present case to either cool or heat the reservoir.

The choice of a suitable reservoir design is a function of the particular case and cannot be defined on an overall basis. Apart from the desired delivery characteristic, a part is played by all the aforementioned parameters.

From the reservoir is formed a delivery apparatus, if all the surfaces not intended for delivery do not have a direct contact with the acceptor medium. They can be covered by surface structures impermeable both for the reservoir components and for the acceptor medium. Another possibility is the preferred embedding of the reservoir in depressions of a carrier material having the same functions as the aforementioned surface structure. The apparatus can optionally be fixed at the point of application and for this purpose external auxiliary means are used, or the apparatus is provided with fixing elements. In the latter case preferably pressure sensitive adhesive areas are provided. Thus, in the case of solid acceptor media, the reservoir itself and therefore the delivery surface can be pressure sensitive adhesive, or the delivery surface is provided with pressure sensitive adhesive areas permitting an unimpeded passage of the active substances. The pressure sensitive adhesive areas can also be provided on other surfaces of the apparatus, if the acceptor media are liquid or gaseous.

Naturally the delivery surface must be protected in connection with the application of the apparatus and this is preferably realized by surface structures, which are impermeable for the reservoir components and which are detachable prior to application.

The materials which can be used for the manufacture of the apparatus are a function of the requirements in the given case and are known to the Expert. The active substances which can be administered with the apparatus are so varied and also known to the Expert, that no exhaustive listing is possible.

BRIEF DESCRIPTION OF THE DRAWING

The invention is described in greater detail hereinafter in non-limitative manner with reference to the drawings, wherein show.

DETAILED DESCRIPTION OF THE INVENTION

Figure 1:
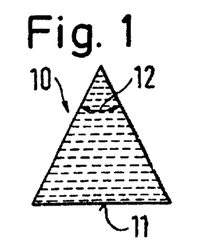
FIGS. 1 to 3 are longitudinal sections through inventive reservoirs.
Figure 2:
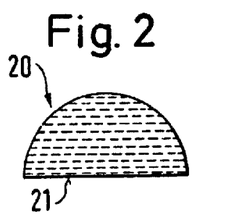

The triangular longitudinal section of FIG. 1 of an inventive reservoir 10 indicates at 11 the section through the delivery surface. The associated reservoir can e.g. have a conical or pyramidal shape and there is a continuous, non-linear cross-sectional reduction. In addition, 10 can be a section through reservoir shape 40 in FIG. 4 or FIG. 4a. The cross-sectional reduction is here continuous and linear. The desired delivery characteristic can be set by choosing the angle 12. FIG. 2 shows the longitudinal section through a hemispherical reservoir 20 with the delivery surface 21, the only variable geometrical parameter being the diameter of the sphere.

Figure 3:
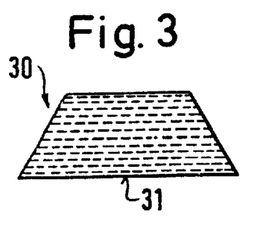
Figure 4:
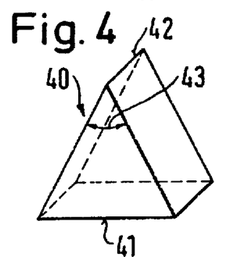
FIG. 4 is a perspective view of one reservoir design.
Figures 4A, 5, 5A, 7, 8:
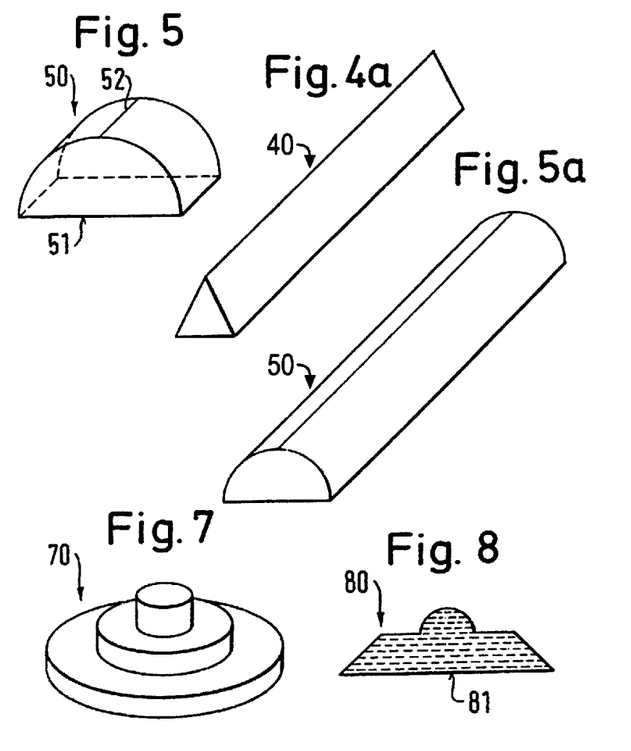
FIG. 4a is a perspective view of a reservoir design according to the principle of FIG. 4.
FIG. 5 is a perspective view of another reservoir design.
FIG. 5a is a perspective view of a reservoir design according to the principle of FIG. 5.
FIG. 7 is a perspective view of a reservoir with a discontinuous cross-sectional reduction.
FIG. 8 is a longitudinal section through a further reservoir with a discontinuous cross-sectional reduction.

Moreover, 50 indicates a section through FIG. 5 and FIG. 5a. In all three cases (FIG. 2, 5 and 5a there is a continuous, non-linear cross-sectional reduction. These reservoir shapes are always appropriate if the delivery quantity is to drop rapidly towards the end of the administration period. The longitudinal section in FIG. 3 applies to a truncated pyramidal reservoir 30. The delivery surface is designated 31. The variation possibilities apply to the height of the truncation and the size of the angle in the apex of the associated pyramid. Here again, the cross-sectional reduction is continuous and non-linear.

Figure 6:
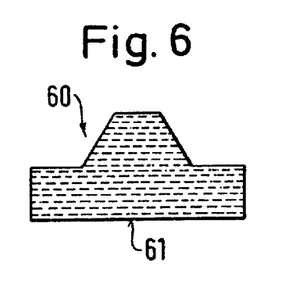
FIG. 6 is a longitudinal section through a reservoir with a discontinuous cross-sectional reduction.

FIG. 4 is a perspective view of a tent-shaped reservoir 40 with 41 as the delivery surface. The variation possibility regarding the length of the upper edge 42, as shown in exemplified manner on the reservoir of FIG. 4a, and the angle 43 determine the possible modifications of this reservoir shape. The cross-sectional reduction is here continuous and linear. The modification of the reservoir shape 50, which is perspectively shown in FIG. 5, can only take place by varying the delivery surface 51 and the length of the vertical line 52 and an example is given in FIG. 5a for the latter case. The reduction of the cross-section is in such cases continuous and non-linear. The design of a reservoir with a discontinuous cross-sectional reduction can be gathered from the longitudinal section 60 in FIG. 6. The reduction is linear if the reservoir has the same longitudinal section at all points. The reservoir delivery surface is 61. The first part of the reservoir above it permits a substantially constant active substance delivery as a result of the geometry. Following a sudden reduction of the cross-section, the cross-section is continuously reduced in the second part of the reservoir.

FIG. 7 also shows a perspective view 70 of a reservoir with a discontinuous cross-sectional reduction, the cross-section in the individual segments remaining constant. This provides a possibility of the stepwise control of the decrease in the active substance delivery. Naturally similar reservoir constructions based on many other different geometrical shapes are possible.

The longitudinal section through a reservoir 80 in FIG. 8 shows the combination of a truncated cone, which forms the delivery surface 81, and a hemisphere. The cross-sectional reduction is discontinuous and non-linear in the individual parts.

Figure 9:
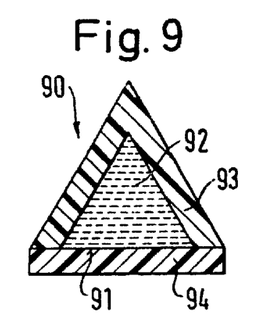
FIG. 9 is a diagrammatic longitudinal section through an inventive apparatus.

In FIG. 9, is the longitudinal section through an inventive apparatus 90 for controlling the active substance delivery. Reservoir 92 corresponds to that shown in FIG. 1 and is provided on the surfaces not intended for active substance delivery with an impermeable layer 93. Delivery surface 91 is covered by a protective layer 94. A pressure sensitive adhesive layer can optionally be provided between the two.

Figure 10:
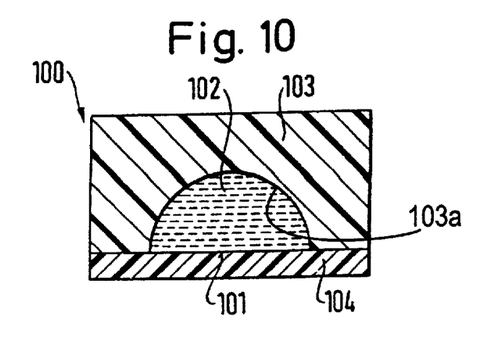
FIG. 10 is a diagrammatic longitudinal section through a further preferred apparatus.

In the case of the longitudinal section through an apparatus 100 in FIG. 10, reservoir 102 according to FIG. 2 is placed in a depression 103a in a carrier material 103. If necessary, the reservoir can be fixed in the depression by an adhesive layer 104. Layer 104 protects the delivery surface 101 prior to use.

Figure 11:
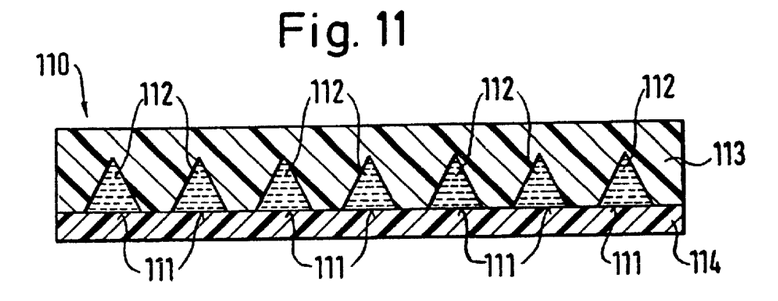
FIG. 11 is a diagrammatic longitudinal section through a further preferred apparatus with several reservoirs.

If for any reason it is necessary to combine several reservoirs in one apparatus, then FIG. 11 provides an example. It shows a longitudinal section through an apparatus 110, in which several conical reservoirs 112 are embedded in the depressions of a carrier material 113. The delivery surfaces 111 are adjacent to a protective layer 114. The geometrical arrangement of the reservoirs with respect to one another can be subject to numerous variants and is a function of practical requirements.

Figure 12:
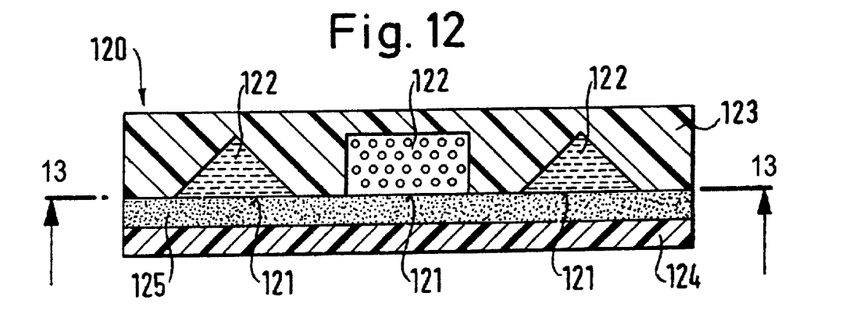
FIG. 12 is a diagrammatic longitudinal section through an apparatus for two different active substances.
Figure 13:
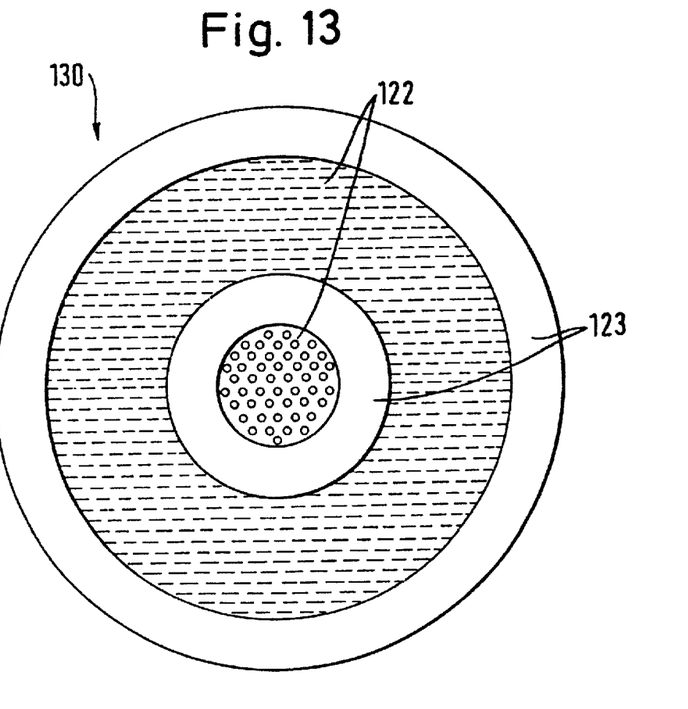
FIG. 13 is a cross-section along line 13—13 in FIG. 12.

FIG. 12 provides an example for the combination of two reservoirs in one apparatus, a longitudinal section through an apparatus 120 being shown. The reservoirs 122 are once again embedded in a carrier material 123. The central reservoir has no cross-sectional reductions and contains a first active substance delivered according to the known release characteristic. In the second reservoir, which surrounds the first in circular manner and has a triangular longitudinal section, is incorporated a second active substance, which is to be released in a controlled, decreasing manner. Delivery surfaces 121 are in contact with a pressure sensitive adhesive layer 125, which is covered by a protective layer 124. FIG. 13 shows the cross-section along line 13—13 of the apparatus 130. It is easy to see the arrangement of reservoirs 121 in carrier material 123, the central cylindrical reservoir of the first active substance being surrounded in circular manner by the reservoir of the second active substance.

Figure 14:
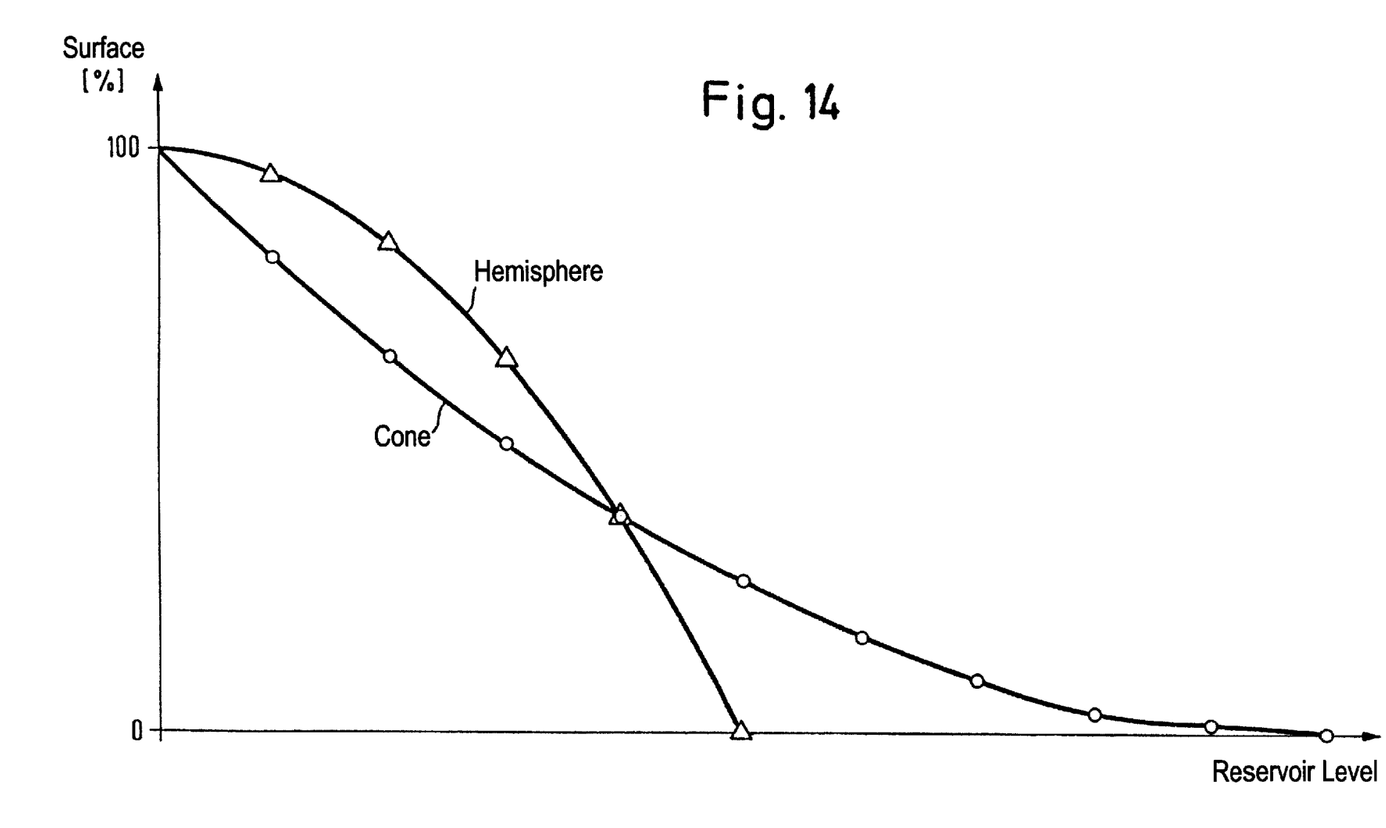
FIG. 14 is a graph of the cross-sectional decrease in the case of a cone and hemisphere.

FIG. 14 graphically shows the cross-sectional reduction in the case of conical and hemispherical reservoirs. It is clear that the two geometrical shapes have completely different decrease characteristics. In the case of a cone there is a slow reduction, whereas in the case of the hemisphere the initial rate is much higher and then it rapidly drops. In both cases the delivery surface is of the same size and the cone angle is 53°.

Figure 15:
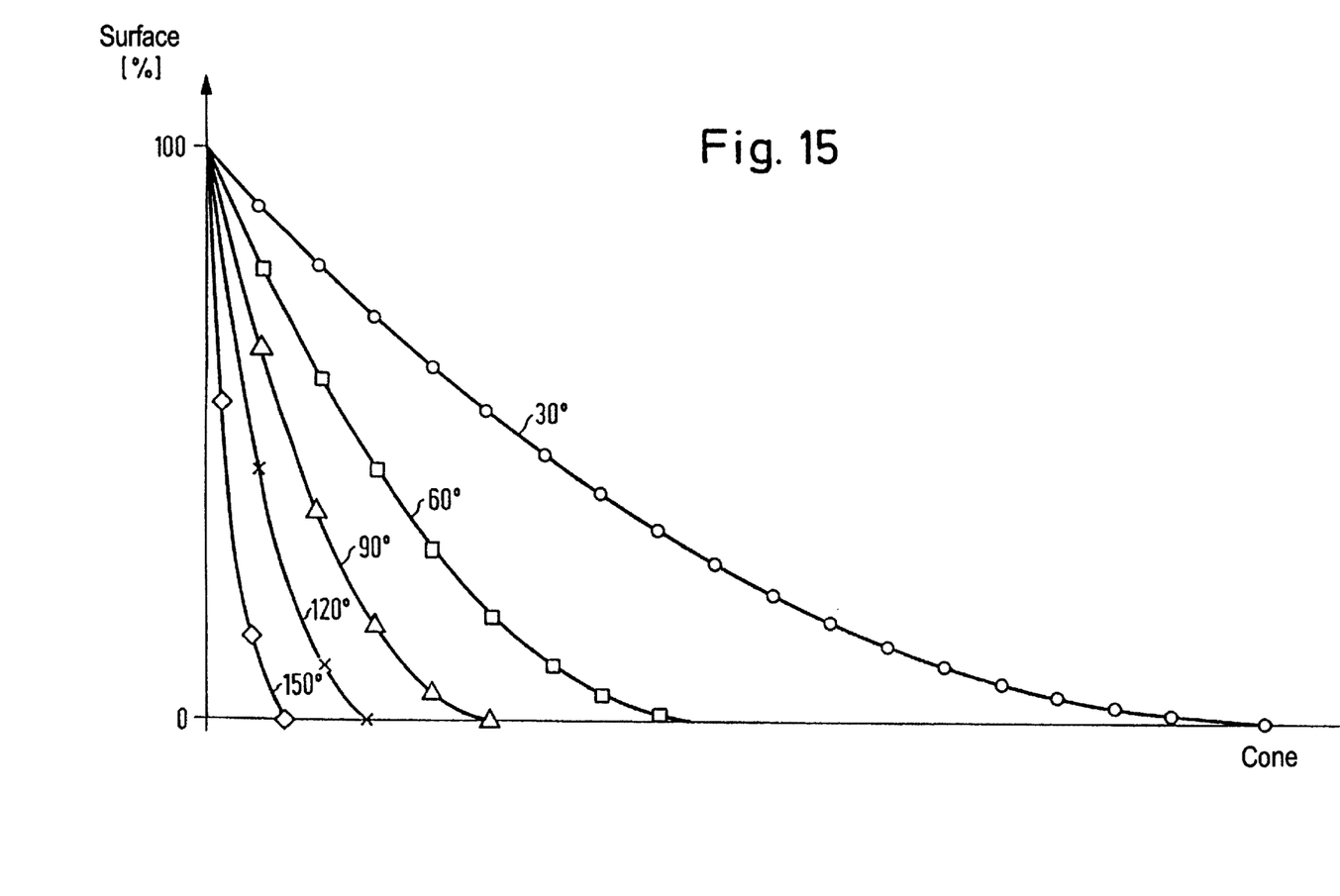
FIG. 15 is a graph of the cross-sectional decrease in the case of a cone and as a function of the cone angle.

The modification to the decreasing surface area characteristic of the cross-section in the case of cones with the same delivery surface as a function of the cone angle can be gathered from FIG. 15. It can be seen that through the choice of angle, virtually any random decreasing characteristic can be obtained.

EXAMPLE

From 3 PVC parallelepipeds with an edge length of 40×40 mm and a height of 24 mm are drilled
a) a cylinder
b) a stepped cylinder (the lower cylinder half only has half the diameter of the upper cylinder half) and
c) a truncated cone in which all the holes in a depth of 20 mm have an opening on the parallelepiped surface of 314 $mm^2$ and the smaller surface of the truncated cone is 14.1 mm. Into the thus obtained holes is introduced melted polyethylene glycol 6000 (PEG 6000) up to approximately 3 mm below the edge. After solidifying the PEG 6000 in the testpieces, further melted PEG 6000 is introduced until an approximately 2 mm high protuberance has formed on the testpiece. The test substance which protrudes after cooling is removed with the aid of a knife down to the upper edge of the testpiece.

The release of the PEG 6000 in water is determined according to the "paddle-over-disc" method of USP XX. The testpiece is removed from the bath every 30 minutes and weighed after careful drying.

Test Conditions

Paddle-over-disc apparatus: SOTAX AT 6 (Sotax AG, Basle)
Release medium: 1000 ml of demineralized water
Temperature: 35° C.
Stirring speed: 50 rpm
Stirring height over testpiece: 15 mm Results The following release rates were measured: flow (g/h):
Cylindrical testpiece (comparison test):

The release rate (flow) from a cylindrical testpiece is constant for approximately 4 hours at approximately 1.8 g/h and then rapidly drops to zero.

In the case of the stepped-cylindrical testpiece with two steps, up to about 2 hours after the start of the test there is a constant release rate of approximately 1.8 g/h. There is then a rapid drop in the release rate corresponding to reaching the step to 0.3 g/h, which remains constant for about 1 hour and then drops to zero after clearing the second step.

In the case of the truncated cone-shaped reservoir, the release rate, measured-as the flow in g/h, drops uniformly from approximately 1.8 g/h at the start of the test to zero within 4 hours, the decrease taking place continuously, or in other words the decrease curve of the flow, plotted against the test time, is essentially a straight line.

Figure 16:
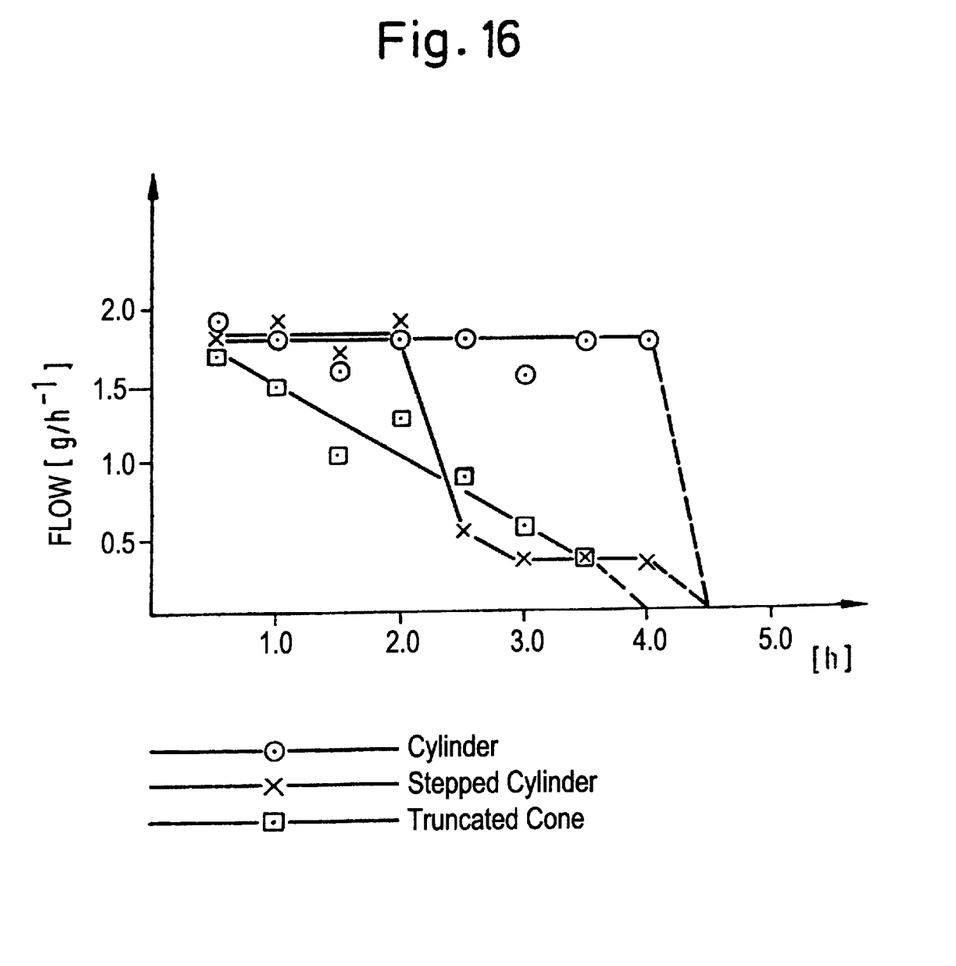
FIG. 16 is a graph of the plotting of the flow against the time according to the example.

The results of the test are shown diagrammatically in FIG. 16.

The drawings are of an examplified nature and are not intended to have a restrictive effect.

What is claimed is:
1. A transdermal therapeutic apparatus, the apparatus comprising at least one reservoir for controlled transdermal delivery of at least one active substance through a delivery surface, wherein the active substance is active in human and veterinary medicine, cosmetic or pest control; wherein the delivery surface is a pressure sensitive adhesive; wherein the amount of active substance delivered is controlled in geometrically planned, time-dependent manner by a geometrically shaped reservoir for the active substance by which at least one cross-sectional surface of the reservoir taken parallel to the delivery surface is smaller in area than the area of the delivery surface, wherein the delivery surface has a maximum extension in one direction up to 100 times the extension in the direction at right angles thereto and wherein the geometrically shaped reservoir is provided with a geometric shape selected from the group consisting of a cone, truncated cone, pyramid, truncated pyramid, hemisphere, tent-shaped, stepped cylinder and cylinder for producing delivery of the active substance which is a function of time dependent upon the geometry of the geometrically shaped reservoir.

2. An apparatus according to claim 1, wherein the reduction in surface area between the reservoir delivery surface and the cross-sectional reservoir surface taken parallel thereto is continuous with increasing distance from the delivery surface.

3. An apparatus according to claim 1, wherein the reduction in surface area between the reservoir delivery surface and the cross-sectional reservoir surface taken parallel thereto is discontinuous with increasing distance from the delivery surface.

4. An apparatus according to claim 1, wherein the reduction in surface area between the reservoir delivery surface and the cross-sectional reservoir surface taken parallel thereto is linear with increasing distance from the delivery surface.

5. An apparatus according to claim 1, wherein the reduction in surface area between the reservoir delivery surface and the cross-sectional reservoir surface taken parallel thereto is non-linear with increasing distance from the delivery surface.

6. An apparatus according to claim 1, wherein the reservoir has no symmetrical elements.

7. An apparatus according to claim 1, wherein the reservoir has a delivery surface having a maximum extension in one direction amounting to 100 times the extension in the direction at right angles thereto.

8. An apparatus according to claim 1, wherein each reservoir is provided with a different geometrical configuration.

9. An apparatus according to claim 1, wherein the entire surface of the reservoir, except the delivery surface, is provided with at least one layer impermeable to the reservoir components.

10. An apparatus according to claim 1, wherein the apparatus is provided with depressions to receive at least part of the reservoirs being fixed by at least one surface, other than the delivery surface, within the depressions.

11. A transdermal therapeutic apparatus comprising at least one reservoir for controlled transdermal delivery of at least one active substance through a delivery surface, wherein the active substance is active in human and veterinary medicine, cosmetic or pest control, wherein the delivery surface is a pressure sensitive adhesive; wherein the amount of active substance delivered is controlled in geometrically planned, time-dependent manner by a geometrically shaped reservoir for the active substance by which at least one cross-sectional surface of the reservoir taken parallel to the delivery surface is smaller in area than the area of the delivery surface, provided that individual cross-sectional surfaces are not enlarged with increasing distance from the delivery surface, wherein the delivery surface has a maximum extension in one direction up to 100 times the extension in the direction at right angles thereto and wherein the geometrically shaped reservoir is provided with a geometric shape selected for the group consisting of a cones truncated cone, pyramids truncated pyramid, hemisphere, tent-shaped, stepped cylinder and cylinder for producing delivery of the active substance which is a function of time dependent upon the geometry of the geometrically shaped reservoir.

12. A transdermal therapeutic apparatus comprising at least one reservoir for controlled transdermal delivery of at least one active substance through a delivery surface, wherein the active substance is active in human and veterinary medicine, cosmetic or pest control, wherein the delivery surface is a pressure sensitive adhesive; wherein the amount of active substance delivered is controlled in geometrically planned, time-dependent manner by a geometrically shaped reservoir for the active substance by which at least one cross-sectional surface of the reservoir taken parallel to the delivery surface is smaller in are than the area of the delivery surface, wherein the delivery surface has a maximum extension in one direction up to to 100 times the extension in the direction at right angles thereto, provided that individual cross-sectional surfaces are not enlarged with increasing distance from the delivery surface, and wherein the geometrically shaped reservoir is provided with a geometric shape selected from the group consisting of a cone, truncated cone, pyramid, truncated pyramid, hemisphere, tent-shaped, stepped cylinder and cylinder for producing delivery of the active substance which is a function of time dependent upon the geometry of the geometrically shaped reservoir.

13. A device of claim 12, wherein the entire surface of the reservoir, except the pressure sensitive adhesive, is provided with at least one layer impermeable to the reservoir components.

14. A device of claim 12, wherein the pressure sensitive adhesive is provided with a protective detachable surface structure having at least one layer and being impermeable to the components of the reservoir.

15. A transdermal therapeutic apparatus consisting of at least one reservoir for controlled transdermal delivery of at least one active substance through a delivery surface, wherein the active substance is active in human and veterinary medicine, cosmetic or pest control; wherein the delivery surface is a pressure sensitive adhesive; wherein the amount of active substance delivered is controlled in geometrically planned, time-dependent manner by a geometrically shaped reservoir for the active substance by which at least one cross-sectional surface of the reservoir taken parallel to the delivery surface is smaller in are than the area of the delivery surface, wherein the delivery surface has a maximum extension in one direction up to to 100 times the extension in the direction at right angles thereto, and wherein the geometrically shaped reservoir is provided with a geometric shape selected from the group consisting of a cone, truncated cone, pyramid, truncated pyramid, hemisphere, tent-shaped, stepped cylinder and cylinder for producing delivery of the active substance which is a function of time dependent upon the geometry of the geometrically shaped reservoir.

16. A transdermal therapeutic apparatus, the apparatus comprising at least one reservoir for controlled transdermal delivery of at least one medicament through a delivery surface, wherein the delivery surface is a pressure sensitive adhesive; wherein the amount of medicament delivered decreases over time of use; wherein at least one cross-sectional surface of the reservoir taken parallel to the delivery surface is smaller in area than the area of the delivery surface, wherein the delivery surface can have a maximum extension in one direction and this can be up to 100 times the extension in the direction at right angles thereto, and wherein the reservoir is provided with a shape selected from the group consisting of a cone, truncated cone, pyramid, truncated pyramid, hemisphere, tent-shaped, stepped cylinder and cylinder.

17. A method for the manufacture of a transdermal therapeutic apparatus, the apparatus comprising at least one reservoir of reservoir material optionally containing solvents or dispersants, for controlled transdermal delivery of at least one reservoir for controlled transdermal delivery of at least one active substance through a delivery surface, wherein the active substance is active in human and veterinary medicine, cosmetic or pest control; wherein the delivery surface is pressure sensitive adhesive; wherein the amount of active substance delivered is controlled in geometrically planned time-dependent manner by a geometrically shaped reservoir for the active substance by which at least one cross-sectional surface of the reservoir taken parallel to the delivery surface is smaller in area of the delivery surface, wherein the delivery surface has a maximum extension in one direction up to 100 times the extension in the direction at right angles thereto, and wherein the geometrically shaped reservoir is provided with a geometric shape selected from the group consisting of a cone, truncated cone, pyramid, truncated pyramid, hemisphere, tent-shaped, stepped cylinder and cylinder for producing delivery of the active substance which is a function of time dependence upon the geometry of the geometrically shaped reservoir; said method comprising forming the reservoir in a corresponding mold by cooling a melt of the reservoir material, evaporating solvents or dispersants, hot or cold pressing the reservoir material, profile extrusion, or crosslinking polymer components by means of radiation or heat, and subsequently laminating, spraying or dipping to provide an impermeable envelope covering all the surfaces, except the delivery surface, or producing in a depression in a carrier material corresponding to the desired reservoir shape.

18. A method according to claim 17, wherein the depression in the carrier material for at least partial reception of a reservoir is produced by deep-drawing or stamping, or by shaping the carrier material.

* * * * *